United States Patent [19]

Ohmori et al.

[11] Patent Number: 4,604,482

[45] Date of Patent: Aug. 5, 1986

[54] PROCESSES FOR PRODUCING α-FLUOROACRYLIC ACID ESTERS AND α-FLUOROACRYLIC ACID FLUORIDE

[75] Inventors: Akira Ohmori, Ibaraki; Shoji Takaki, Toyonaka; Takahiro Kitahara, Settsu, all of Japan

[73] Assignee: Daikin Kogyo Co., Ltd., Osaka, Japan

[21] Appl. No.: 655,078

[22] Filed: Sep. 27, 1984

[30] Foreign Application Priority Data

Oct. 4, 1983 [JP] Japan ................................ 58-186326

[51] Int. Cl.$^4$ ..................... C07C 67/317; C07C 51/58
[52] U.S. Cl. .................................. 560/213; 260/544 F
[58] Field of Search ...................... 260/544 F; 560/213

[56] References Cited

U.S. PATENT DOCUMENTS

| | | | |
|---|---|---|---|
| 2,440,090 | 4/1948 | Howk | 260/544 F |
| 3,075,002 | 1/1963 | Sedlak | 560/210 |
| 3,213,134 | 10/1965 | Morin | 260/544 F |
| 3,654,245 | 4/1972 | Kometani et al. | 560/213 |
| 3,706,795 | 12/1972 | Lichstein et al. | 260/544 F |
| 4,357,282 | 11/1982 | Anderson et al. | 260/544 C |

OTHER PUBLICATIONS

Clark, N. G., *Modern Organic Chemistry* (1964) pp. 90, 223 Oxford Univ. Press, Publ.
Conant, James Bryant et al., The Chemistry of Organic Compounds, 4th Ed. (1955) MacMillan, Publ., p. 137.
Patai, Saul, The Chemistry of Acyl Halides (1972), pp. 44–45, Interscience, Publ.
Devaquet, Alain J. P. et al., *Chemical Abstracts*, vol. 85 (1976), #142,429a. See also p. 4380CS of vol. 85.

*Primary Examiner*—Natalie Trousof
*Assistant Examiner*—L. Hendriksen
*Attorney, Agent, or Firm*—Larson and Taylor

[57] ABSTRACT

This invention provides a process for preparing an α-fluoroacrylic acid ester characterized by reacting 2,2,3,3-tetrafluorooxetane, a metal halide, an alcohol and a dehalogenating agent. This invention also provides a process for preparing α-fluoroacrylic acid fluoride, $CH_2=CFCOF$, which is an intermediate for preparing the α-fluoroacrylic acid ester.

16 Claims, No Drawings

PROCESSES FOR PRODUCING α-FLUOROACRYLIC ACID ESTERS AND α-FLUOROACRYLIC ACID FLUORIDE

This invention relates to novel processes for producing α-fluoroacrylic acid esters and α-fluoroacrylic acid fluoride from 2,2,3,3-tetrafluorooxetane.

It is known to produce α-fluoroacrylic acid esters by fluorinating an α,α,β-tribromopropionic acid ester with mercury(II) fluoride to obtain α,β-dibromo-α-fluoropropionic acid ester and debrominating the α,β-dibromo-α-fluoropropionic acid ester (Journal of the Chemical Society, Vol. 76, pp. 479–481, 1954), or by fluorinating a monochloroacetic acid ester with potassium fluoride to obtain monofluoroacetic acid ester, reacting the acid ester with dimethyl oxalate and sodium hydride in ether and reacting the resulting product with paraformaldehyde and sodium methoxide (Macromolecules, Vol. 13, pp. 1031–1036, 1980).

The former process requires use of a highly toxic mercury compound and is as low as up to 10% in yield, while the latter process involves preparation of similarly toxic monofluoroacetic acid ester as an intermediate, is about 30% in yield and needs the use of highly inflammable ether as a solvent.

An object of the present invention is to provide a novel process for producing α-fluoroacrylic acid esters which is free of the problems of the conventional processes.

Another object of the invention is to provide a process for preparing an intermediate useful for the preparation of α-fluoroacrylic acid esters.

These objects and other features of the invention will become apparent from the following description.

The present invention provides a process for producing an α-fluoroacrylic acid ester characterized by reacting 2,2,3,3-tetrafluorooxetane, a metal halide, an alcohol and a dehalogenating agent.

The invention further provides a process for preparing an ethylenically unsaturated compound represented by the formula

$$CH_2=CFCOF \quad (I)$$

characterized by reacting 2,2,3,3-tetrafluorooxetane, a metal halide and a dehalogenating agent.

Examples of metal halides useful for the present invention are halides, such as chlorides, bromides and iodides, of alkali metals, Sb, Zn, Mg, Cu, Sn, Fe, Pb, Cd, etc. More specific examples are LiI, NaI, KCl, KBr, KI, SbI$_3$, SbI$_5$, ZnI$_2$, ZnIF, ZnICl, MgI$_2$, CuI, SnI$_4$, FeI$_2$, PbI$_2$, CdI, CdI$_2$ and the like. In view of the solubility in the alcohol, etc. to be used for the reaction of the invention, NaI, ZnFI, ZnI$_2$, KI, ZnICl, MgI$_2$ and the like are preferable. Usually the metal halide is used in an amount of about 0.01 to about 5.0 moles, preferably about 0.1 to about 1.5 moles, per mole of the starting material, i.e. 2,2,3,3-tetrafluorooxetane.

The alcohol to be used for the present invention can be any of aliphatic, alicyclic, aromatic and heterocyclic alcohols. The alcohol may be substituted with at least one halogen atom, such as fluorine, chlorine, bromine or iodine atom. Phenols are similarly usable as alcohols. Examples of aliphatic alcohols are those having 1 to 24 carbon atoms, such as methanol, ethanol, propanol, n-butanol, isobutyl alcohol, sec-butyl alcohol, t-butyl alcohol, n-amyl alcohol, n-dodecyl alcohol, 2,2,2-trifluoroethyl alcohol, 2,2,3,3,3-pentafluoropropyl alcohol, 2,2,3,3-tetrafluoropropyl alcohol, 2-trifluoromethyl-2,3,3,3-tetrafluoropropyl alcohol, 2-trifluoromethyl-3,3,3-trifluoropropyl alcohol, n-tetradecyl alcohol, n-octadecyl alcohol, 2-ethyl-1-hexyl alcohol, 2-chloroethyl alcohol, 2,3-dibromopropyl alcohol and the like. Examples of useful alicyclic alcohols are those having 6 to 20 carbon atoms, such as cyclohexyl alcohol, 2-methylcyclohexyl alcohol, 3-methylcyclohexyl alcohol, 3,3,5-trimethylcyclohexyl alcohol, 4-tertamylcyclohexyl alcohol, 2,4-diamylcyclohexyl alcohol, hydroabietyl alcohol, bornyl alcohol, 1-adamantyl alcohol and the like. Examples of useful aromatic alcohols are phenyl- or phenoxy-substituted C$_{1-4}$ aliphatic alcohols which may be substituted with halogen or nitro on the phenyl ring, such as 1-phenylethyl alcohol, benzyl alcohol, 2-phenoxyethyl alcohol, o-chlorobenzyl alcohol, 2,4,6-trinitrophenylethyl alcohol and the like. Examples of useful heterocyclic alcohols are tetrahydrofurfuryl alcohol, 1,3-dioxolanylmethyl alcohol and the like. Examples of useful phenols are phenol which may be substituted with halogen, C$_{1-4}$ alkyl, cyclohexyl or nitro on the phenyl ring, such as phenol, o-methylphenol, p-chlorophenol, p-tert-butylphenol, p-cyclohexylphenol, p-nitrophenol and the like. Such alcohol is usually used in an amount of about 1 to about 100 moles, preferably about 1 to about 5 moles, per mole of the starting material, i.e. 2,2,3,3-tetrafluorooxetane. As will be described later, the alcohol constitutes the ester group of the desired α-fluoroacrylate, so that a suitable alcohol is selected for use in accordance with the kind of desired product.

Any dehalogenating agent can be used insofar as the agent has the function of removing two different halogen atoms from two adjacent carbon atoms to form a double bond. Examples of such agents are metals such as Zn, Na, Mg, Sn, Cu, Fe, Li and the like. Among these, Zn is desirable from the viewpoint of reaction velocity. Usually the dehalogenating agent is used in an amount of about 0.1 to about 3 moles, preferably about 1.1 to about 2 moles, per mole of the starting material, i.e. 2,2,3,3-tetrafluorooxetane.

According to the present invention, the desired α-fluoroacrylate can be obtained in a single stage by reacting specified amounts of 2,2,3,3-tetrafluorooxetane, metal halide, alcohol and dehalogenating agent as placed in a reactor at the same time, or by adding 2,2,3,3-tetrafluorooxetane to the mixture of specified amounts of metal halide, alcohol and dehalogenating agent for reaction. When required, the reaction may be carried out with use of a solvent. It is preferable to use polar solvents such as acetone, dimethylformamide, acetonitrile, dimethylacetamide and the like. The reaction temperature is about 0° to about 150° C., preferably about 40° to about 60° C. The reaction usually takes about 0.5 to about 3 hours.

The desired α-fluoroacrylate can be prepared also by the following process.

First, 2,2,3,3-tetrafluorooxetane, a metal halide and a dehalogenating agent are reacted to obtain a compound represented by the formula

$$CH_2=CFCOF \quad (I)$$

For this reaction, the metal halide is used in an amount of about 0.01 to about 5 moles, preferably about 0.1 to about 1.5 moles, and the dehalogenating agent is used in an amount of about 0.1 to about 3 moles, preferably about 1.1 to about 2 moles, per mole of the oxetane. The reaction may be carried out with use of a solvent such as dimethylformamide, acetonitrile, acetone, dimethylacetamide. The reaction is conducted usually at a temperature of about 30° to about 60° C. for about 0.5 to about 3 hours.

Next, the compound of the formula (I) is reacted with the alcohol exemplified above, giving the desired α-fluoroacrylic acid ester of the formula $$CH_2=CFCOOR \qquad (II)$$

wherein R is a residue obtained by removing a hydroxyl group of the alcohol used. The residue represented by R includes alkyl having 1 to 24 carbon atoms which may be substituted with at least one halogen atom, alicyclic groups having 6 to 20 carbon atoms, phenyl- or phenoxysubstituted $C_{1-4}$ alkyl which may be substituted with halogen or nitro on the phenyl ring, tetrahydrofurfuryl, 1,3-dioxolanylmethyl, phenyl which may be substituted with halogen, $C_{1-4}$ alkyl, cyclohexyl or nitro on the phenyl ring. The alcohol is used usually in an amount of about 1 to about 100 moles, preferably about 1 to about 5 moles, per mole of the compound of the formula (I). The reaction may be carried out with use of a solvent such as those exemplified above. The reaction is conducted usually at a temperature of about 0° to about 40° C. for about 0.5 to about 3 hours.

mable solvents. The resulting product is purified by a conventional method such as vacuum distillation, etc.

The α-fluoroacrylates of the formula (II) afforded by the present invention can be polymerized by a conventional method of polymerization such as block, suspension, emulsion or solution polymerization. The polymers have the advantage of being higher in softening point, thermal decomposition temperature and weather resistance and less susceptible to cracking than methacrylate polymers and are useful as materials for coating compositions, optical fiber claddings, resist for microfabrication, etc.

The invention will be described in greater detail with reference to the following examples.

EXAMPLES 1–7

An α-fluoroacrylate was prepared in each example by placing into a five-liter flask an alcohol, solvent, dehalogenating agent, polymerization inhibitor and metal halide listed in Table 1 below, heating the materials at 40° to 60° C. and adding dropwise 520 g of 2,2,3,3-tetrafluorooxetane to the materials over a period of 3 hours with stirring. The resulting ester was isolated by rectification. Table 1 shows the results.

The products obtained in Examples 1 and 3–7 were 45° C./130 mm Hg in boiling point, and the product of Example 2 had a boiling point of 20° C./10 mm Hg.

TABLE 1

| Example | Alcohol | Dehalogenating agent | Polymerization inhibitor | Metal halide | Solvent | α-Fluoro-acrylate (g) | yield (%) |
|---|---|---|---|---|---|---|---|
| 1 | Methanol (300) | Zn (400) | Hydroquinone (5) | NaI (600) | Dimethyl-formamide (2500) | 330 | 80 |
| 2 | Pentafluoro-propanol (300) | Zn (400) | Hydroquinone (5) | NaI (600) | Dimethyl-formamide (2500) | 720 | 81 |
| 3 | Methanol (300) | Mg (146) | Hydroquinone (5) | NaI (600) | Dimethyl-formamide (2500) | 264 | 64 |
| 4 | Methanol (300) | Na (138) | Hydroquinone (5) | KBr (476) | Dimethyl-formamide (2500) | 198 | 48 |
| 5 | Methanol (300) | Zn (400) | Hydroquinone (5) | KI (664) | Acetonitrile (2500) | 281 | 68 |
| 6 | Methanol (300) | Zn (400) | Hydroquinone (5) | NaI (600) | Acetone (2500) | 219 | 53 |
| 7 | Methanol (2800) | Zn (400) | Hydroquinone (5) | NaI (600) | None | 322 | 78 |

Note
The values in the parentheses are charges in gram.

When the α-fluoroacrylic acid ester of the formula (II) or the compound of the formula (I) produced by the foregoing processes of the invention are likely to polymerize, it is desirable to add to the reaction system an agent which is conventionally used for inhibiting radical polymerization. Examples of useful radical polymerization inhibiting agents are hydroquinone, methoxyhydroquinone, t-butylcatechol, sulfur, p-benzoquinone, tetrachloro-para-benzoquinone, diphenyl picryl hydrazyl, verdazyl, amines such as triethylamine, trimethylamine, tributylamine, pyridine, etc. Such agents are used in an amount effective for inhibiting radical polymerization, i.e. in an amount usually of up to several % by weight, preferably about 0.5 to about 5% by weight, based on the α-fluoroacrylate of the formula (II) or the compound of the formula (I).

In this way, α-fluoroacrylates of the formula (II) can be produced in good yields according to the invention without using highly toxic materials or readily inflam-

EXAMPLE 8

(a) Five grams of hydroquinone, 2500 g of dimethylformamide, 300 g of sodium iodide and 400 g of zinc were placed into a five-liter flask and then heated at 40° to 60° C. Subsequently 520 g of 2,2,3,3-tetrafluorooxetane was added dropwise to the materials over a period of 3 hours. The reaction mixture was thereafter distilled at a reduced pressure of 30 mm Hg to collect in a cold trap a fraction boiling at temperatures of up to 60° C., whereby 246 g of α-fluoroacrylic acid fluoride ($CH_2=CFCOF$) was obtained. $^1H$ NMR and $^{19}F$ NMR analyses of the compound gave the following results.

$^1H$ NMR δ=5.66 ppm, d, $J_{cisHF}$=10 Hz, $J_{transHF}$=36 Hz, (acetone-$d_6$) 5.98 ppm, d,d,d, $J_{HH}$=2 Hz $^{19}F$ NMR (external standard $CF_3COOH$, chemical shifts (acetone-$d_6$) upfield from the standard are designated positive) δ=−89.8 ppm, d,d, 41.7 ppm, d,d,d, $J_{FF}$=16 Hz (b) Zinc (400 g) was additionally placed into the flask, and 520 g of 2,2,3,3-tetrafluorooxetane was placed dropwise into the flask in the same manner as above. The reaction mixture was distilled again at a reduced pressure of 30 mm Hg, and a fraction boiling at temperatures of up to 60° C. was collected in a cold trap, giving 238 g of α-fluoroacrylic acid fluoride (compound of the formula (I)).

(c) The two portions of α-fluoroacrylic acid fluoride obtained were combined together, and the combined product was added dropwise to 600 g of methanol over a period of 2.5 hours while maintaining the reaction system at a temperature of up to 15° C. The reaction mixture was thereafter washed with 5% aqueous solution of sodium hydrogencarbonate. The organic layer was distilled to give 465 g of methyl α-fluoroacrylate (boiling at 45° C./130 mm Hg).

EXAMPLES 9-16

α-Fluoroacrylates were prepared in the same manner as in Example 1 except that methanol was replaced by the alcohols listed in Table 2 below. Table 2 also shows the results.

TABLE 2

| Example | Alcohol | B.p. (°C./mm Hg) | Yield (%) |
|---------|---------|------------------|-----------|
| 9 | $CF_3CH_2OH$ | 28/30 | 72 |
| 10 | $HCF_2CF_2CH_2OH$ | 42/12 | 73 |
| 11 | $H(CF_2CF_2)_2CH_2OH$ | 38-42/4 | 70 |
| 12 | cyclohexyl-OH | 53/4 | 55 |
| 13 | phenyl-OH | 43-46/2 | 63 |
| 14 | $C_8F_{17}CH_2CH_2OH$ | 86/4 | 70 |
| 15 | $CCl_3CH_2OH$ | 46/2 | 69 |
| 16 | 3,3,5-trimethyl-cyclohexanol | 48/2 | 77 |

We claim:

1. A process for producing an α-fluoroacrylic acid ester comprising providing a mixture comprising 2,2,3,3-tetrafluorooxetane, a metal halide, an alcohol and a dehalogenating agent to effect reaction thereof to produce an α-fluoroacrylic acid ester.

2. A process as defined in claim 1 wherein the metal halide comprises a chloride, bromide or iodide of an alkali metal, Sb, Zn, Mg, Cu, Sn, Fe, Pb or Cd.

3. A process as defined in claim 1 wherein the metal halide is used in an amount of about 0.01 to about 5.0 moles per mole of the 2,2,3,3-tetrafluorooxetane.

4. A process as defined in claim 1 wherein the alcohol is selected from the group consisting of aliphatic alcohols having 1 to 24 carbon atoms which may be substituted with at least one halogen atom, alicyclic alcohols having 6 to 20 carbon atoms, phenyl or phenoxy-substituted $C_{1-4}$ aliphatic alcohols which may be substituted with halogen or nitro on the phenyl ring, tetrahydrofurfuryl alcohol 1,3-dioxolanylmethyl alcohol and phenol which may be substituted with halogen, $C_{1-4}$ alkyl, cyclohexyl or nitro on the phenyl ring.

5. A process as defined in claim 1 wherein the alcohol is used in an amount of about 1 to about 100 moles per mole of the 2,2,3,3-tetrafluorooxetane.

6. A process as defined in claim 1 wherein the dehalogenating agent comprises a material selected from the group consisting of Zn, Na, Mg, Sn, Cu, Fe and Li.

7. A process as defined in claim 1 wherein the dehalogenating agent is used in an amount of about 0.1 to about 3 moles per mole of the 2,2,3,3-tetrafluorooxetane.

8. A process as defined in claim 1 wherein the reaction is carried out at about 0° to about 150° C.

9. A process as defined in claim 1 wherein the reaction is carried out in a solvent.

10. A process for preparing a compound represented by the formula $$CH_2=CFCOF \qquad (I)$$

which comprises providing a mixture comprising 2,2,3,3-tetrafluorooxetane, a metal halide and a dehalogenating agent to effect reaction thereof to form a compound represented by said formula.

11. A process as defined in claim 10 wherein the metal halide comprises a chloride, bromide or iodide of an alkali metal, Sb, Zn, Mg, Cu, Sn, Fe, Pb or Cd.

12. A process as defined in claim 10 wherein the metal halide is used in an amount of about 0.01 to about 5 moles per mole of the 2,2,3,3-tetrafluorooxetane.

13. A process as defined in claim 10 wherein the dehalogenating agent comprises a material selected from the group consisting of Zn, Na, Mg, Sn, Cu, Fe and Li.

14. A process as defined in claim 10 wherein the dehalogenating agent is used in an amount of about 0.1 to about 3 moles per mole of the 2,2,3,3-tetrafluorooxetane.

15. A process as defined in claim 10 wherein the reaction is carried out at about 30° to about 60° C.

16. A process as defined in claim 10 wherein the reaction is carried out in a solvent.